United States Patent [19]

Isoda et al.

[11] 4,239,903
[45] Dec. 16, 1980

[54] 2-AMINOTETRALIN DERIVATIVES AND PROCESS FOR PRODUCING THE SAME

[75] Inventors: Sumiro Isoda; Munefumi Kanao; Yoshifumi Ichikawa; Takeshi Hashizume; Kiyoshi Irie; Yoshio Kasai, all of Tokyo, Japan

[73] Assignee: Daiichi Seiyaku Co., Ltd., Tokyo, Japan

[21] Appl. No.: 906,510

[22] Filed: May 16, 1978

[30] Foreign Application Priority Data

May 17, 1977 [JP] Japan .................. 52/56837

[51] Int. Cl.$^3$ ............................................. C07C 69/84
[52] U.S. Cl. ...................................... 560/73; 560/65; 560/70; 560/71; 560/72; 560/107; 260/340.3; 260/340.5 R; 424/282; 424/308
[58] Field of Search ............... 560/107, 73, 74, 65, 560/67, 70, 71, 72; 260/340.3, 340.5 R, 340.6

[56] References Cited

U.S. PATENT DOCUMENTS 2,112,899  4/1938  Lott et al. .......................... 560/107

FOREIGN PATENT DOCUMENTS 39-4617 of 1964 Japan .

OTHER PUBLICATIONS

Coles, Harold et al., "Local Anesthetics Containing the ac-Tetrahydro-beta-naphthylamine Pressor Group," J. Am. Chem. Soc., (1936), vol. 58, pp. 1989-1990.
McDermed, John D. et al., "Synthesis and Pharmacology of Some 2-Aminotetralins, Dopamine Receptor Agonists", J. of Medical Chem., (1975), vol. 18, (4), pp. 362-367.

Primary Examiner—Natalie Trousof
Assistant Examiner—L. Hendriksen
Attorney, Agent, or Firm—Sughrue, Rothwell, Mion, Zinn and Macpeak

[57] ABSTRACT

Compounds, which have antispasmodic effects, represented by the following formula (I)

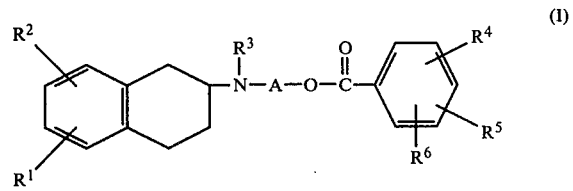

wherein $R^1$ and $R^2$, which may be the same or different, each represents a hydrogen atom, an alkoxy group or, when taken together, $R^1$ and $R^2$ represent an alkylenedioxy group; $R^3$ represents a hydrogen atom, an alkyl group or a cycloalkyl group; $R^4$, $R^5$ and $R^6$, which may be the same or different, each represents a hydrogen atom, an alkoxy group, an alkyl group, a halogen atom, a hydroxyl group or, when two of $R^4$, $R^5$ and $R^6$ are taken together, they represent an alkylenedioxy group; and A represents a straight or branched chain alkylene group having 2 to 10 carbon atoms or an alkylene group having 2 to 10 carbon atoms and interrupted with an oxygen atom forming an ether bond therein, and the therapeutically useful acid-addition salts thereof; and a process for producing the same.

12 Claims, No Drawings

2-AMINOTETRALIN DERIVATIVES AND PROCESS FOR PRODUCING THE SAME

BACKGROUND OF THE INVENTION

1. Field of the Invention

This invention relates to novel 2-aminotetralin derivatives and the therapeutically useful acid addition salts thereof. More specifically, this invention relates to 2-aminotetralin derivatives and the therapeutically useful acid addition salts thereof having excellent antispasmodic activity and to processes for their production.

2. Description of the Prior Art

Reserpine and reserpine analogues have been described in the art as providing various pharmacological effects.

More specifically, reserpine analogues containing phenethylamine moieties are disclosed in A. Linder et al, *Journal of Medicinal Chemistry*, Vol. 6, p. 97 (1963) as providing pharmacological effects such as blood pressure depression, spasmolysis and adrenolysis.

Further, U.S. Pat. No. 3,254,112, discloses aralkylaminoesters of nuclear substituted benzoic acids useful as spasmolytic agents.

Of these prior art known compounds having therapeutically active effects, all can be considered to be derivatives of phenethylamine compounds and as far as it is known, no compounds with a 2-aminotetralin moiety are known or have been described in the art.

SUMMARY OF THE INVENTION

This invention provides 2-aminotetralin derivatives represented by the following general formula (I):

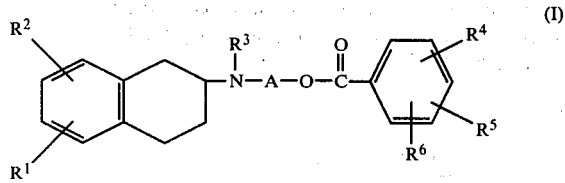

wherein $R^1$ and $R^2$, which may be the same or different, each represents a hydrogen atom, an alkoxy group or, when taken together, $R^1$ and $R^2$ represent an alkylenedioxy group; $R^3$ represents a hydrogen atom, an alkyl group or a cycloalkyl group; $R^4$, $R^5$ and $R^6$, which may be the same or different, each represents a hydrogen atom, an alkoxy group, an alkyl group, a halogen atom, a hydroxyl group or, when two of $R^4$, $R^5$ and $R^6$ are taken together, they represent an alkylenedioxy group; and A represents a straight or branched chain alkylene group having 2 to 10 carbon atoms or an alkylene group having 2 to 10 carbon atoms and interrupted with an oxygen atom forming an ether bond therein, and the therapeutically useful acid addition salts thereof, which have excellent antispasmodic effects.

DETAILED DESCRIPTION OF THE INVENTION

The terms "alkyl" and "alkoxy" as used herein for $R^1$ to $R^6$ refer to those groups having 1 to 6 carbon atoms which may be straight chain or branched chain groups.

The term "cycloalkyl" as used herein for $R^3$ refers to those groups having 4 to 7 carbon atoms.

The term "alkylenedioxy" as used herein for $R^1$ and $R^2$, and two of $R^4$, $R^5$ and $R^6$ refers to those groups having 1 to 3 carbon atoms.

In the present invention, representative 2-aminotetralin derivatives represented by the general formula (I) above and the therapeutically useful salts thereof include, for example, the following compounds and the therapeutically useful acid addition salts thereof.

(1). N-Ethyl-N-[4-(3,4-dimethoxybenzoyloxy)butyl]-1,2,3,4-tetrahydro-2-naphthylamine hydrochloride (hereinafter referred to as Compound A)

(2). N-Ethyl-N-[6-(3,4-dimethoxybenzoyloxy)hexyl]-1,2,3,4-tetrahydro-2-naphthylamine hydrochloride (hereinafter referred to as Compound B)

(3). N-Ethyl-N-[4-(3,4-dimethoxybenzoyloxy)butyl]-5-methoxy-1,2,3,4-tetrahydro-2-naphthylamine hydrochloride (4). N-[4-(3,4-Dimethoxybenzoyloxy)butyl]-6-methoxy-1,2,3,4-tetrahydro-2-naphthylamine hydrochloride (5). N-Ethyl-N-[2-(3,4-dimethoxybenzoyloxy)ethyl]-6-methoxy-1,2,3,4-tetrahydro-2-naphthylamine hydrochloride (6). N-Methyl-N-[4-(3,4-dimethoxybenzoyloxy)butyl]-6-methoxy-1,2,3,4-tetrahydro-2-naphthylamine hydrochloride (7). N-Ethyl-N-[3-(3,4-dimethoxybenzoyloxy)propyl]-6-methoxy-1,2,3,4-tetrahydro-2-naphthylamine hydrochloride (8). N-Ethyl-N-[3-(3,4-dimethoxybenzoyloxy)-2,2-dimethylpropyl]-6-methoxy-1,2,3,4-tetrahydro-2-naphthylamine hydrochloride (9). N-Ethyl-N-{2-[2-(3,4-dimethoxybenzoyloxy)ethoxy]ethyl}-6-methoxy-1,2,3,4-tetrahydro-2-naphthylamine hydrochloride (10). N-Ethyl-N-[4-(3,4-dimethoxybenzoyloxy)butyl]-6-methoxy-1,2,3,4-tetrahydro-2-naphthylamine hydrochloride (hereinafter referred to as Compound C)

(11). N-Ethyl-N-[4-(benzoyloxy)butyl]-6-methoxy-1,2,3,4-tetrahydro-2-naphthylamine hydrochloride (12). N-Ethyl-N-[4-(3,4-dihydroxybenzoyloxy)butyl]-6-methoxy-1,2,3,4-tetrahydro-2-naphthylamine hydrochloride (13). N-Ethyl-N-[4-(4-methoxybenzoyloxy)butyl]-6-methoxy-1,2,3,4-tetrahydro-2-naphthylamine hydrochloride (14). N-Ethyl-N-[4-(3-methoxybenzoyloxy)butyl]-6-methoxy-1,2,3,4-tetrahydro-2-naphthylamine hydrochloride (15). N-Ethyl-N-[4-(4-ethoxybenzoyloxy)butyl]-6-methoxy-1,2,3,4-tetrahydro-2-naphthylamine hydrochloride (16). N-Ethyl-N-[4-(4-propoxybenzoyloxy)butyl]-6-methoxy-1,2,3,4-tetrahydro-2-naphthylamine hydrochloride (17). N-Ethyl-N-[4-(4-methylbenzoyloxy)butyl]-6-methoxy-1,2,3,4-tetrahydro-2-naphthylamine hydrochloride (18). N-Ethyl-N-[4-(3-methoxy-4-ethoxybenzoyloxy)butyl]-6-methoxy-1,2,3,4-tetrahydro-2-naphthylamine hydrochloride (19). N-Ethyl-N-[4-(3,4-dichlorobenzoyloxy)butyl]-6-methoxy-1,2,3,4-tetrahydro-2-naphthylamine hydrochloride (20). N-Ethyl-N-[4-(3,4-methylenedioxybenzoyloxy)butyl]-6-methoxy-1,2,3,4-tetrahydro-2-naphthylamine hydrochloride (21). N-Ethyl-N-[4-(2,6-dimethoxybenzoyloxy)butyl]-6-methoxy-1,2,3,4-tetrahydro-2-naphthylamine hydrochloride (22). N-Ethyl-N-[4-(3,4,5-trimethoxybenzoyloxy)butyl]-6-methoxy-1,2,3,4-tetrahydro-2-naphthylamine methanesulfonate (23). N-Ethyl-N-[4-(3,4,5-triethoxybenzoyloxy)butyl]-6-methoxy-1,2,3,4-tetrahydro-2-naphthylamine hydrochloride (24). N-Ethyl-N-[6-(3,4-dimethoxybenzoyloxy)hexyl]-6-methoxy-1,2,3,4-tetrahydro-2-naphthylamine hydrochloride (hereinafter referred to as Compound D)

(25). N-Ethyl-N-[8-(3,4-dimethoxybenzoyloxy)octyl]-6-methoxy-1,2,3,4-tetrahydro-2-naphthylamine hydrochloride (26). N-Ethyl-N-[10-(3,4-dimethoxybenzoyloxy)decyl]-6-methoxy-1,2,3,4-tetrahydro-2-naphthylamine hydrochloride (27). N-Propyl-N-[4-(3,4-dimethoxybenzoyloxy)butyl]-6-methoxy-1,2,3,4-tetrahydro-2-naphthylamine hydrochloride (hereinafter referred to as Compound E)

(28). N-Isopropyl-N-[4-(3,4-dimethoxybenzoyloxy)butyl]-6-methoxy-1,2,3,4-tetrahydro-2-naphthylamine hydrochloride (hereinafter referred to as Compound L)

(29). N-Cyclohexyl-N-[4-(3,4-dimethoxybenzoyloxy)butyl]-6-methoxy-1,2,3,4-tetrahydro-2-naphthylamine hydrochloride (30). N-Ethyl-N-[4-(3,4-dimethoxybenzoyloxy)butyl]-6-ethoxy-1,2,3,4-tetrahydro-2-naphthylamine hydrochloride (31). N-Ethyl-N-[4-(3,4-dimethoxybenzoyloxy)butyl]-6-propoxy-1,2,3,4-tetrahydro-2-naphthylamine hydrochloride (32). N-Ethyl-N-[4-(3,4-dimethoxybenzoyloxy)butyl]-5,8-dimethoxy-1,2,3,4-tetrahydro-2-naphthylamine hydrochloride (33). N-Ethyl-N-[4-(3,4-dimethoxybenzoyloxy)butyl]-6,7-dimethoxy-1,2,3,4-tetrahydro-2-naphthylamine hydrochloride (hereinafter referred to as Compound F)

(34). N-Ethyl-N-[6-(3,4-dimethoxybenzoyloxy)hexyl]-6,7-dimethoxy-1,2,3,4-tetrahydro-2-naphthylamine hydrochloride (hereinafter referred to as Compound G)

(35). N-Ethyl-N-[4-(3,4-dimethoxybenzoyloxy)butyl]-6,7-methylenedioxy-1,2,3,4-tetrahydro-2-naphthylamine hydrochloride (36). N-Ethyl-N-[4-(3,4-dimethoxybenzoyloxy)butyl]-7-methoxy-1,2,3,4-tetrahydro-2-naphthylamine hydrochloride (hereinafter referred to as Compound H)

(37). N-Ethyl-N-[4-(3,4-dimethoxybenzoyloxy)butyl]-8-methoxy-1,2,3,4-tetrahydro-2-naphthylamine hydrochloride (hereinafter referred to as Compound K)

(38). N-Ethyl-N-[6-(3,4-dimethoxybenzoyloxy)hexyl]-8-methoxy-1,2,3,4-tetrahydro-2-naphthylamine hydrochloride A preferred class of the compounds of the general formula (I) is those represented by the formula (I')

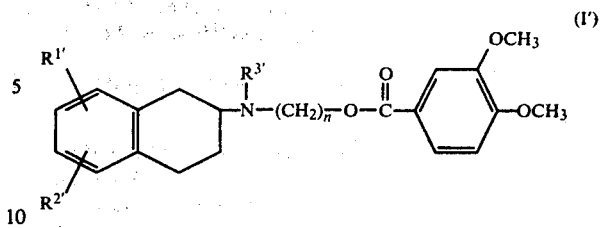

wherein $R^{1'}$ and $R^{2'}$, which may be the same or different, each represents a hydrogen atom or an alkoxy group; $R^{3'}$ represents an alkyl group; and n is either 4 or 6, and the therapeutically useful acid-addition salts thereof.

The above-described 2-aminotetralin derivatives of the general formula (I) of the present invention can be synthesized by various processes. One of the most general processes is described below.

A compound represented by the general formula (I) above where $R^1$, $R^2$, $R^3$ and A are the same as defined above and $R^4$, $R^5$ and $R^6$ are the same as defined above except that $R^4$, $R^5$ and $R^6$ do not represent a hydroxy group [hereinafter a compound represented by the general formula (Ia)] can be prepared by heating a compound represented by the following general formula (II)

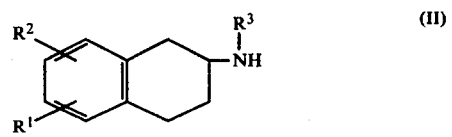

wherein $R^1$, $R^2$ and $R^3$ are the same as defined above, together with a compound represented by the following general formula (III)

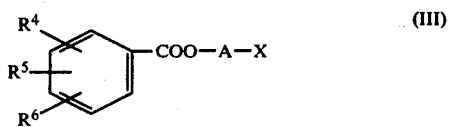

wherein $R^4$, $R^5$ and $R^6$ are the same as defined above except that $R^4$, $R^5$ and $R^6$ are not a hydroxy group, A is the same as defined above, and X represents a halogen atom, in the presence of a base such as sodium carbonate, anhydrous potassium carbonate, etc. in an organic solvent inert to both compounds represented by the general formulae (II) and (III), such as acetone, methyl ethyl ketone, acetonitrile, benzene, etc. to obtain the end product, a compound represented by the general formula (Ia). Additionally, when X is a halogen atom other than iodine, addition of sodium iodide can be used to accelerate the reaction in a smooth manner.

Alternatively, a compound represented by the general formula (Ia) above can be prepared by reacting a compound represented by the general formula (II) as described above with a compound represented by the following general formula (IV)

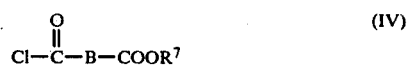

wherein $R^7$ represents an alkyl group having 1 to 6 carbon atoms, and B represents an alkylene group having two less carbon atoms than A, in the presence of a base such as triethylamine, trimethylamine, etc. in an organic solvent inert to the compounds represented by the general formulae (II) and (IV), such as benzene, toluene, xylene, chloroform, etc. to produce a compound represented by the following general formula (V)

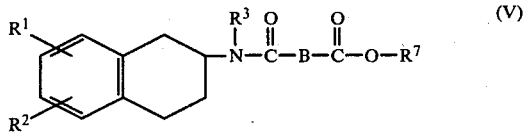

wherein $R^1$, $R^2$, $R^3$, $R^7$ and B are the same as defined above. Subsequently, this compound represented by the general formula (V) is reacted with lithium aluminum hydride in an organic solvent such as diethyl ether, tetrahydrofuran, dioxane, etc. to produce a compound represented by the following general formula (VI)

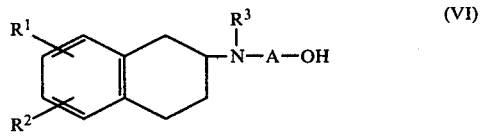

wherein $R^1$, $R^2$, $R^3$ and A are the same as defined above. This compound represented by the general formula (VI) is then reacted with the compound represented by the following general formula (VII)

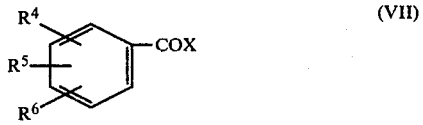

wherein $R^4$, $R^5$ and $R^6$ are the same as defined above except that $R^4$, $R^5$ and $R^6$ are not a hydroxy group and X is as defined above in the absence of or in the presence of a base such as triethylamine, trimethylamine, etc. in an organic solvent inert to the compounds represented by the general formulae (VI) and (VII), such as benzene, toluene, xylene, chloroform, etc. to obtain the product, a compound represented by the general formula (Ia).

A compound represented by the general formula (I) wherein $R^4$, $R^5$ and $R^6$ each represents a hydroxy group [hereinafter a compound represented by the general formula (Ib)] can be obtained by conducting the above-described processes wherein in the starting compound represented by the general formula (III) or (VII) wherein $R^4$, $R^5$ and $R^6$ each represents a hydroxy group, and A and X are the same as defined above the hydroxy group is protected with a protective group such as a benzyl group, and after the reaction, the protective group is eliminated through a catalytic reduction so as not to split the ester bond.

The above processes are described hereinafter in greater detail.

The starting material represented by the general formula (II) can be prepared typically by reacting a tetralone compound of the general formula (VIII)

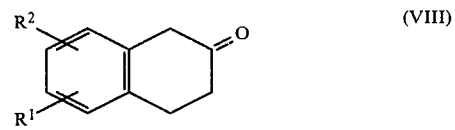

wherein $R^1$ and $R^2$ are as defined above, with a compound of the general formula (IX)

wherein $R^3$ is as defined above, in the presence of a catalyst such as Raney nickel or platinum oxide in a hydrogen atmosphere. Examples of suitable tetralone compounds represented by the general formula (VIII) are 5-methoxy-2-tetralone (described in *J. Chem. Soc.* 1942, 689), 6-methoxy-2-tetralone (described in *Org. Syn.* 51 109), 6,7-dimethoxy-2-tetralone [described in *J. Chem. Soc.*(c) 1967 228 and *Ann.* 685 141 (1965)], 6,7-methylenedioxy-2-tetralone (described in *Bull. Soc. Chem. France* 1967 4469), 7-methoxy-2-tetralone [described in *J. Am. Chem. Soc.* 71 3857 (1949)], 8-methoxy-2-tetralone (described in *J. Chem. Soc.* 1958 409), 2-tetralone (described in *Org. Syn. Coll.* vol. 4 903) and the like.

Some of the compounds of the general formula (II) are known compounds as disclosed in *J. Chem. Soc.* 1965 2636, but other compounds of the general formula (II) can also be prepared in the same manner as disclosed in the above literature.

Suitable starting materials represented by the general formula (III) are disclosed in U.S. Pat. No. 3,254,112.

The reaction between the compound of the general formula (II) and the compound of the general formula (III) can be advantageously carried out at a temperature ranging from room temperature (about 25° C.) to about 140° C. for a period of about 3 to about 50 hours using an equimolar amount of the compounds of the general formulae (II) and (III), but either of the compounds of the general formulae (II) and (III) can be used in a smaller or larger amount than the other without any adverse affects on the reaction. The base is preferably used in an amount of from about 1 to about 2 mols per mol of the compound of the general formula (II).

In an alternative process for preparing the compound of the general formula (I), the starting material represented by the general formula (IV) can be prepared in accordance with the procedure described in *J. Org. Chem.* 24, 1497 (1959).

The reaction between the compound of the general formula (II) and the compound of the general formula (IV) can be carried out at a temperature ranging from about room temperature (about 25° C.) to about 140° C. for a period of about 1 to about 25 hours using, advantageously, an equimolar amount of the compounds of the general formulae (II) and (IV), but again either of these compounds can be used in a smaller or larger proportion than the other without any adverse affects. The base preferably is used in an amount of from about 1 to about 2 mols per mol of the compound of the general formula (II).

The subsequent reduction of the compound of the general formula (V) thus obtained with lithium aluminum hydride can be carried out, after distilling off the solvent used, at a temperature of about 0° C. to about 110° C. for a period of about 1 to about 8 hours. The lithium aluminum hydride can be preferably used in an amount of from about 1.5 to about 4 mols per mol of the compound of the general formula (V).

The resulting reaction mixture is then treated with an aqueous medium such as aqueous tetrahydrofuran to decompose the remaining lithium aluminum hydride and filtered to remove Al(OH)$_3$), and the filtrate is concentrated and extracted with an organic solvent such as chloroform. The organic extract containing the compound of the general formula (VI) is then reacted with the compound of the general formula (VII) at a temperature of from about room temperature to about 140° C. to obtain the desired compound of the general formula (I).

The compound of the general formula (VII) can easily be prepared by reacting a corresponding carboxylic acid with thionyl chloride or phosphorus pentachloride in a conventional manner.

In addition to the above-described process, a compound represented by the general formula (I) can also be prepared using various other processes, for example, as shown by processes (A), (B), (C) or (D) schematically illustrated below. In each formula shown below, $R^1$, $R^2$, $R^3$, $R^4$, $R^5$, $R^6$, X and A are the same as defined hereinbefore with respect to the general formula (I).

Also, the compounds represented by the general formula (I) can form an acid addition salt. Suitable acid addition salts are the therapeutically useful acid addition salts formed from inorganic acids such as hydrochloric acid, hydrobromic acid, sulfuric acid, phosphoric acid, nitric acid, etc., and organic acids such as tartaric acid, oxalic acid, citric acid, methanesulfonic acid, p-toluenesulfonic acid, lactic acid, malic acid, maleic acid, etc.

The usefulness of the compounds represented by the general formula (I) above and the therapeutically useful acid addition salts thereof, hereinafter collectively the compounds of the present invention, is described in detail below.

The 2-aminotetraline derivatives of the present invention exhibit a potent antispasmodic effect on smooth muscle organs such as the stomach and the intestines. The compounds of the present invention are extremely useful as medicines particularly acting on the lower digestive tract. Table 1 below shows the effect of representative compounds of the present invention on colonic contraction caused by stimulating the pelvic nerve in anesthesized dogs. N-Ethyl-N-[4-(3,4-dimethoxybenzoyloxy)butyl]-3-(4-methoxyphenyl)-2-propylamine

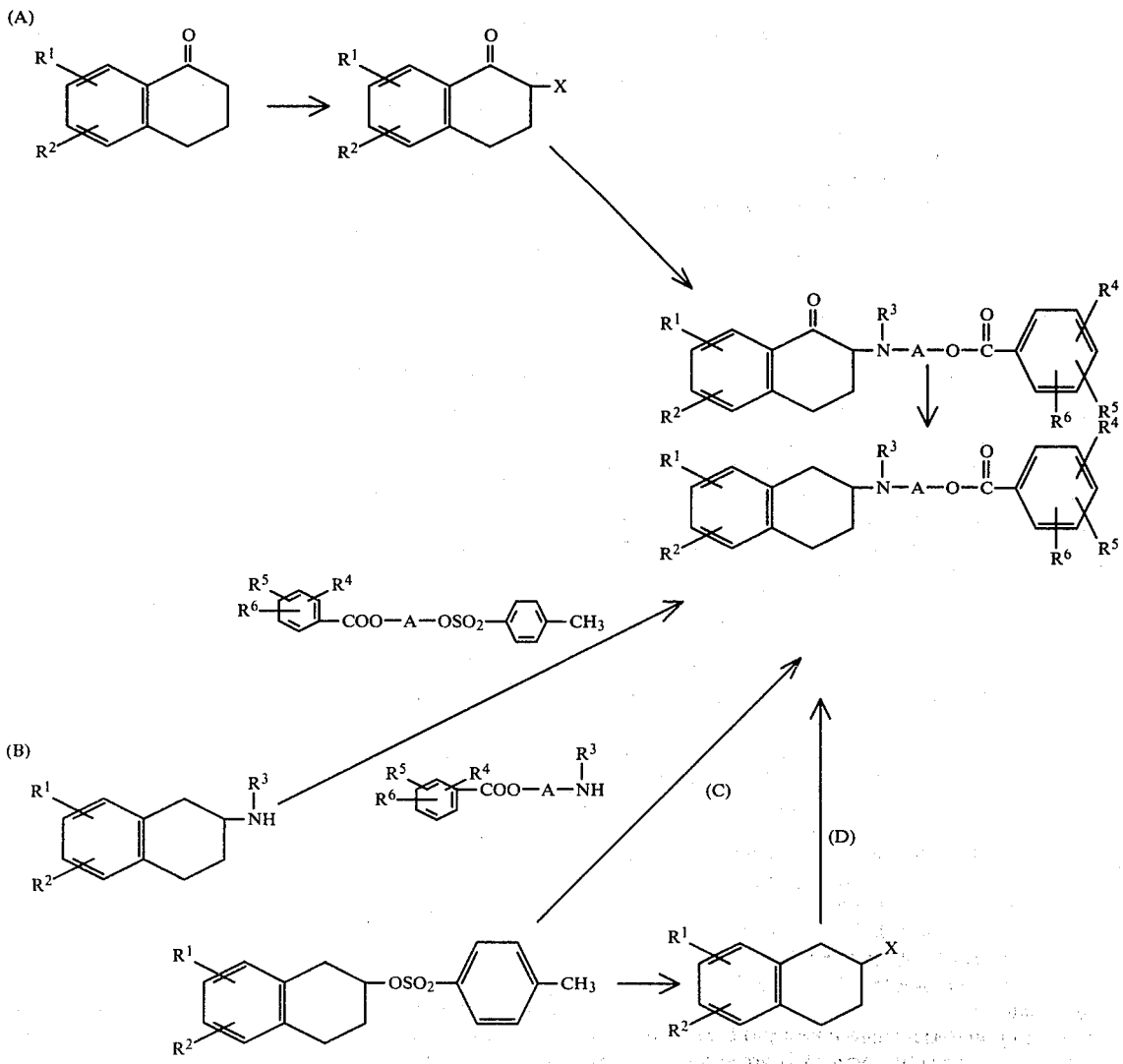

hydrochloride (hereinafter referred to as "mebeverine") known as an antispasmodic for the lower digestive tract was used as a reference.

TABLE 1

Effect of Compounds (100 μg/kg, i.v.) on Colonic Contraction Caused by Stimulation of Pelvic Nerve in Anesthetized Dogs

| Compound | % Inhibition of Colonic Contraction (100 μg/kg, i.v.) |
|---|---|
| Compound A | 27.9 |
| Compound B | 56.0 |
| Compound C | 20.0 |
| Compound D | 54.7 |
| Compound E | 22.4 |
| Compound F | 63.8 |
| Compound G | 54.2 |
| Compound H | 30.9 |
| Compound K | 40.0 |
| Mebeverine | 22.0 | i.v. = intravenous

The values shown in Table 1 were obtained according to the following method [as disclosed in *European Journal of Pharmacology*, 18, pp. 1–14 (1972)].

Mongrel dogs of both sexes weighing 8–15 kg were used.

After intravenous anesthesizing with pentobarbital in a dose of 30 mg/kg, the animals were fixed on their back and subjected to ventrotomy along the midline of the lower abdomen. After a rubber balloon filled with water was inserted into the descending colon via the anus, 100 μg/kg of each compound was injected intravenously and changes in the internal pressure of the balloon were recorded on a polygraph through a low pressure transducer. Electric stimulation (rectangular wave, 50 cps in frequency, 1 msec in duration, 4 V in voltage) was applied to the pelvic nerve for 5 seconds every three minutes. The percent inhibition of the colonic contraction was calculated according to the following relationship.

$$\text{Percent Inhibition} = 100 - \frac{\text{Average Contraction for 30 Minute Period after Drug Injection}}{\text{Average Contraction before Drug Injection}} \times 100$$

Table 2 below shows the acute toxicity, effect on colonic motility stimulated by neostigmine, and safety margins of representative compounds of the present invention and mebeverine in rats.

TABLE 2

Acute Toxicity (LD$_{50}$), Effect on Colonic Motility (ED$_{50}$) and Safety Margin (LD$_{50}$/ED$_{50}$) in Rats

| | p.o. (mg/kg) | | | i.v. (mg/kg) | | |
|---|---|---|---|---|---|---|
| Compound | LD$_{50}$ | ED$_{50}$ | LD$_{50}$/ED$_{50}$ | LD$_{50}$ | ED$_{50}$ | LD$_{50}$/ED$_{50}$ |
| Mebeverine | 1540 | 30.0 | 51 | 17.7 | 0.151 | 117 |
| Compound C | >2000 | 14.4 | >139 | 19.3 | 0.169 | 114 |
| Compound L | 1540 | 17.3 | 89 | Slightly soluble | 0.173 | — |
| Compound E | 707 | 17.3 | 41 | 22.3 | 0.173 | 129 |
| Compound D | 2830 | 5.5 | 515 | 35.3 | 0.046 | 767 |
| Compound F | 1540 | 5.5 | 280 | 16.2 | 0.025 | 648 |
| Compound B | >2000 | 5.5 | >364 | 17.7 | 0.086 | 206 |
| Compound G | 561 | 1.7 | 330 | 17.5 | 0.020 | 885 | p.o. = oral administration
i.v. = intravenous administration

The method for testing the effect on colonic motility was as follows.

Male STD Wistar strain rats weighing 300–400 g were used. After intraperitoneally anesthesizing the rats with 1 g/kg (i.p.) of ethyl carbamate, the rats were fixed on their back and a rubber balloon filled with water was inserted into the descending colon via the anus. Changes in the internal pressure of the balloon were recorded on a polygraph via a low pressure transducer. In order to maintain a constant colonic motility, neostigmine was continuously subcutaneously injected into each rat at a rate of 90 μg/kg/hr (s.c.). The test drugs were each dissolved in distilled water at various concentrations and administered into the stomach through an oral catheter in a volume of 0.2 ml/100 g of body weight. The dose at which an inhibition of colonic motility was observed in 50% of the rats used was expressed as the ED$_{50}$.

The data shown in Tables 1 and 2 above demonstrate that the compounds of the present invention are useful medicines with a potent antispasmodic effect and low toxicity. The compounds of the present invention are further characterized by the following property. The compounds of the present invention have selectively stronger antispasmodic effect on the lower part of the digestive tract than on the upper part of the digestive tract, in contrast to conventional anticholinergic antispasmodics which act non-selectively on the digestive tract. The evidence for this selectivity is exemplified by the results shown for representative compounds of the present invention in Table 3. In Table 3, the s.ID$_{50}$ and c.ID$_{50}$ values represent the doses causing 50% inhibition of the contractile response of the stomach to vagal stimulation and 50% inhibition of the colonic contraction by pelvic nerve stimulation, respectively, in dogs. These values and their ratios (s.ID$_{50}$/c.ID$_{50}$) indicate that these compounds have higher selectivity than mebeverine, as is clear from Table 3.

TABLE 3

Selectivity of Antispasmodic Effect

| Compound | s.ID$_{50}$ (μg/kg i.v.) | c.ID$_{50}$ (μg/kg i.v.) | s.ID$_{50}$/c.ID$_{50}$ |
|---|---|---|---|
| Compound D | 614 | 83 | 7.40 |
| Compound F | 266 | 57 | 4.67 |
| Mebeverine | 823 | >300 | <2.74 |

The determination of gastric motility was carried out according to the method described in *European Journal of Pharmacology*, 18, pp. 1–14 (1972).

More specifically mongrel dogs of both sexes weighing 8–15 kg were used. After anesthesizing the animals with 30 mg/kg (i.v.) of pentobarbital, the animals were fixed on their back and a midline incision was made in the upper abdomen. A rubber balloon filled with water was inserted into the stomach through an incision in the greater curvature. Changes in internal pressure of the balloon were recorded on a polygraph via a low pressure transducer. Electric stimulation (rectangular wave, 20 cps in frequency, 1 msec in duration, 8 V in voltage) was applied to the vagus nerve for 10 seconds every three minutes. The percent inhibition of the contractile response of the stomach was calculated from the relationship shown above.

c. $ID_{50}$ values were determined by the same method as was used for Table 1. Subacute toxicity: No significant abnormal behavior nor pathological disorder on blood, urine and the organs was observed when orally administering Compound D to JCL-SD strain rats, 6 weeks old, in a daily dose up to 200 mg/kg during a 5-week period.

The compounds of the present invention can be advantageously administered via oral route in dosage forms such as tablets, capsules, and the like, at a dosage level of about 30 mg to about 200 mg/day for an adult human, in a single dose or divided into 3 to 4 doses.

The present invention will now be illustrated in more detail by reference to the following Examples. Unless otherwise indicated herein, all parts, percents, ratios and the like are by weight.

EXAMPLE 1

1.85 g of N-ethyl-1,2,3,4-tetrahydro-2-naphthylamine, 3.9 g of 4-iodobutyl 3,4-dimethoxybenzoate, 1.1 g of sodium carbonate and 40 ml of methyl ethyl ketone were mixed and heated at reflux for 60 hours. The reaction solution was concentrated under reduced pressure, and water was added to the residue, followed by extraction with chloroform. The chloroform layer was washed with water, dried over anhydrous sodium sulfate, and concentrated under reduced pressure. The residual oily material was purified through silica gel chromatography. To this was added an ethanolic solution of hydrogen chloride having a concentration of about 18%, and the mixture was concentrated under reduced pressure. The product was crystallized from an acetone-diethyl ether mixed solution and the crystals formed were collected through filtration. Recrystallization from ethanol-diethyl ether yielded 2.3 g of colorless, powdery N-ethyl-N-[4-(3,4-dimethoxybenzoyloxy)butyl]-1,2,3,4-tetrahydro-2-naphthylamine hydrochloride having a melting point of 119°–121° C.

Elemental Analysis: Calcd. for $C_{25}H_{33}NO_4 \cdot HCl \cdot 1/2 H_2O$ (%): C, 65.70; H, 7.71; N, 3.06. Found (%): C, 65.77; H, 7.72; N, 3.06.

EXAMPLE 2

(i) 28.0 g of 6-methoxy-2-tetralone, 200 ml of a 19% ethylamine-ethanol solution, 2.2 g of platinum oxide and 10 ml of absolute ethanol were mixed and the mixture was irradiated with infrared light in the presence of hydrogen to cause a catalytic hydrogenation to occur. After absorption of hydrogen had been completed, the platinum oxide catalyst was filtered off from the reaction solution and the filtrate was concentrated under reduced pressure, followed by extraction with chloroform. The chloroform layer obtained was washed with water, dried over anhydrous sodium sulfate, and concentrated under reduced pressure. The residue obtained was dissolved in an ethanolic solution of hydrogen chloride having a concentration of about 18% and the solution was concentrated under reduced pressure. Acetone was added to the residue obtained to cause crystallization. The crystals were collected through filtration and recrystallized from ethanol-diethyl ether to give 29.7 g of N-ethyl-6-methoxy-1,2,3,4-tetrahydro-2-naphthylamine hydrochloride as colorless crystals having a melting point of 231°–232° C.

Elemental Analysis: Calcd. for $C_{13}H_{19}NO \cdot HCl$ (%): C, 64.58; H, 8.34; N, 5.79; Cl, 14.67. Found (%): C, 64.62; H, 8.55; N, 6.04; Cl, 14.44.

(ii) 2.0 g of N-ethyl-6-methoxy-1,2,3,4-tetrahydro-2-naphthylamine hydrochloride produced as described in (i) above and 20 ml of a 2 N-sodium hydroxide aqueous solution were mixed and followed by extraction with chloroform. After the choroform layer was dried and concentrated under reduced pressure, the free base obtained was mixed with 3.1 g of 4-iodobutyl 3,4-dimethoxybenzoate, 0.9 g of sodium carbonate and 40 ml of methyl ethyl ketone, and the mixture was heated for 60 hours at reflux. The reaction solution was concentrated under reduced pressure, and water was added to the residue, followed by extraction with chloroform. The chloroform layer was washed with water, dried over anhydrous sodium sulfate, and concentrated under reduced pressure. The residual oily product was purified through silica gel chromatography to obtain N-ethyl-N-[4-(3,4-dimethoxybenzoyloxy)butyl]-6-methoxy-1,2,3,4-tetrahydro-2-napthylamine as an oily product. To this product, an ethanolic solution of hydrogen chloride having a concentration of about 18% was added and the solution was concentrated under reduced pressure. The residue obtained was dissolved in acetone, and diethyl ether was added to the solution. The solution was left at a temperature of about 2° to 3° C. to form crystals. The crystals were collected through filtration, and recrystalized from an acetone-diethyl ether mixed solution to obtain 2.65 g of N-ethyl-N-[4-(3,4-dimethoxybenzoyloxy)butyl]-6-methoxy-1,2,3,4-tetrahydro-2-naphthylamine hydrochloride as colorless crystals having a melting point of 139°–140° C.

Elemental Analysis: Calcd. for $C_{26}H_{35}NO_5 \cdot HCl$ (%): C, 65.33; H, 7.59; N, 2.93. Found (%): C, 65.84; H, 7.46; N, 2.97.

EXAMPLE 3

(i) 4.7 g of lithium aluminum hydride and 200 ml of anhydrous tetrahydrofuran were mixed, and to this mixture was added dropwise a mixed solution of 10 g of N-acetyl-6-methoxy-1,2,3,4-tetrahydro-2-naphthylamine and 100 ml of anhydrous tetrahydrofuran. After the mixture was stirred for 0.5 hour at room tempertature (about 25° C.) and heated for 4 hours at reflux, a mixture of 4.7 ml of water in 50 ml of tetrahydrofuran was added dropwise to this solution under cooling with ice, and then 4.7 ml of a 15% sodium hydroxide aqueous solution and 14 ml of water were added dropwise to the solution in this order. Precipitated unsoluble material was removed by filtration and the filtrate was concentrated under reduced pressure. The residue obtained was extracted with chloroform, and the chloroform layer was washed with water, dried over anhydrous sodium sulfate and concentrated under reduced prossure. To the residual oily product was added an ethanolic solution of hydrogen chloride having a concentration of about 18% and the solution was concentrated under reduced pressure. After adding acetone to the residue, the crystals formed were collected and recrystallized from an ethanol-diethyl ether solution to obtain 8.9 g of N-ethyl-6-methoxy-1,2,3,4-tetrahydro-2-naphthylamine hydrochloride as colorless needles having a melting point of 231°–232° C. Physical data such as melting point, infrared spectra, etc. for this product corresponded to those for the product obtained by Example 2 (i).

(ii) 3.1 g of 6-chlorohexyl 3,4-dimethoxybenzoate, 1.4 g of sodium iodide, 2.0 g of sodium carbonate and 80 ml of methyl ethyl ketone were added to the free base compound, obtained from 2.0 g of N-ethyl-6-methoxy-1,2,3,4-tetrahydro-2-naphthylamine hydrochloride produced as described in (i) above, and the mixture was heated for 90 hours at reflux. The reaction solution was concentrated under reduced pressure and the residue was extracted with chloroform. The chloroform layer was washed with water, dried over anhydrous sodium sulfate and concentrated under reduced pressure to obtain an oily product. The oily product was purified through silica gel chromatography to obtain N-ethyl-N-[6-(3,4-dimethoxybenzoyloxy)-hexyl]-6-methoxy-1,2,3,4-tetrahydro-2-naphthylamine as a pale-yellow oily product. After the oily product was dissolved in an ethanolic solution of hydrogen chloride having a concentration of about 18%, the solution was concentrated under reduced pressure. The residue obtained was dissolved in acetone, diethyl ether was added to the solution, and the solution was left at a temperature of about 2° to 3° C. for crystals to form. The crystals were collected by filtration and recrystallized from a mixed solution of acetone and diethyl ether to obtain 1.3 g of N-ethyl-N-[6-(3,4-dimethoxybenzoyloxy)hexyl]-6-methoxy-1,2,3,4-tetrahydro-2-naphthylamine hydrochloride as colorless crystals having a melting point of 119°–120° C.

Elemental Analysis: Calcd. for $C_{28}H_{39}NO_5 \cdot HCl$ (%): C, 66.45; H, 7.97; N, 2.77. Found (%): C, 66.63, H, 8.04; N, 2.73.

EXAMPLE 4

(i) A mixture of 7.4 g of anhydrous aluminum chloride and 100 ml of anhydrous methylene chloride was cooled at −50° C. and to the mixture was added dropwise a solution of 5.9 g of 3,4-dimethoxyphenylacetyl chloride and 30 ml of anhydrous methylene chloride. Subsequently, while stirring the solution vigorously, ethylene was forced fed into the solution for 15 minutes. Then, after stirring the solution for 3.5 hours at room temperature (about 25° C.), the reaction solution was cooled in an ice-water bath and 40 ml of water was added dropwise thereto. The methylene chloride layer was washed with a 2 N-HCl aqueous solution, water, a saturated sodium bicarbonate aqueous solution and water in order, dried over anhydrous sodium sulfate and concentrated under reduced pressure to obtain a oily product. To the oily product were added 25 ml of a 19% ethylamine-ethanol solution, 10 ml of absolute ethanol and 0.25 g of platinum oxide, and the solution was catalytically hydrogenated. After take up of hydrogen had been completed, the platinum oxide catalyst was removed by filtration and the filtrate was concentrated under reduced pressure. To the residue obtained was added an ethanolic solution of hydrogen chloride having a concentration of about 18% and then the resulting solution was concentrated under reduced pressure. After adding acetone to the residue, the crystals formed were collected by filtration and dissolved in a 2 N-NaOH aqueous solution. After extraction with chloroform, the chloroform layer was washed with water, dried over anhydrous potassium hydroxide and concentrated under reduced pressure. The residue obtained was purified through alumina column chromatography. To the purified reaction solution was added an ethanolic solution of hydrogen chloride having a concentration of about 18% and the solution was concentrated under reduced pressure to obtain crystals. The crystals were recrystallized from a mixed solution of absolute ethanol and isopropyl alcohol to obtain 1.12 g of N-ethyl-6,7-dimethoxy-1,2,3,4-tetrahydro-2-naphthylamine hydrochloride as colorless needles having a melting point of 246°–248° C. (decomp.).

Elemental Analysis: Calcd. for $C_{14}H_{21}NO_2 \cdot HCl$ (%): C, 61.87; H, 8.16; N, 5.15. Found (%): C, 61.46; H, 8.06; N, 5.14.

(ii) Using the procedures described in Example 3 (ii), 400 mg of N-ethyl-N-[4-(3,4-dimethoxybenzoyloxy)-butyl]-6,7-dimethoxy-1,2,3,4-tetrahydro-2-naphthylamine hydrochloride was obtained as colorless crystals having a melting point of 107°–109° C., starting from 390 mg of N-ethyl-6,7-dimethoxy-1,2,3,4-tetrahydro-2-naphthylamine hydrochloride, 500 mg of 4-chlorobutyl 3,4-dimethoxybenzoate, 270 mg of sodium iodide, 200 mg of anhydrous sodium carbonate and 30 ml of methyl ethyl ketone.

Elemental Analysis: Calcd. for $C_{27}H_{37}NO_6 \cdot HCl$ (%): C, 63.83; H, 7.54; N, 2.76. Found (%): C, 64.19; H, 7.63; N, 2.60.

EXAMPLE 5

Using the procedures in Example 3 (ii), 7.0 g of N-ethyl-N-[6-(3,4-dimethoxybenzoyloxy)hexyl]-6,7-dimethoxy-1,2,3,4-tetrahydro-2-naphthylamine hydrochloride was obtained as colorless needles having a melting point of 102°–105° C., starting from 6.0 g of N-ethyl-6,7-dimethoxy-1,2,3,4-tetrahydro-2-naphthylamine hydrochloride, 9.2 g of 6-chlorohexyl 3,4-dimethoxybenzoate, 4.6 g of sodium iodide, 3.3 g of anhydrous sodium carbonate and 150 ml of methyl ethyl ketone.

Elemental Analysis: Calcd. for $C_{29}H_{41}NO_6 \cdot HCl$ (%): C, 64.97; H, 7.90; N, 2.61. Found (%): C, 64.94; H, 7.91; N, 2.70.

EXAMPLE 6

Using the procedures described in Example 3 (ii), 1.0 g of N-ethyl-N-[6-(3,4-dimethoxybenzoyloxy)hexyl]-1,2,3,4-tetrahydro-2-naphthylamine hydrochloride was obtained as a colorless oily product, starting from 1.86 g of N-ethyl-1,2,3,4-tetrahydro-2-naphthylamine hydrochloride, 2.9 g of 6-chlorohexyl 3,4-dimethoxybenzoate, 1.45 g of sodium iodide, 1.02 g of anhydrous sodium carbonate and 30 ml of methyl ethyl ketone.

Elemental Analysis: Calcd. for $C_{27}H_{37}NO_4 \cdot HCl$ (%): C, 68.28; H, 7.48; N, 2.95. Found (%): C, 67.73; H, 8.16; N, 3.39.

EXAMPLE 7

Using the procedures described in Example 3 (ii), 1.6 g of N-ethyl-N-{2-[2-(3,4-dimethoxybenzoyloxy)ethoxy]ethyl}-6-methoxy-1,2,3,4-tetrahydro-2-naphthylamine hydrochloride was obtained as a colorless oily product, starting from 1.91 g of N-ethyl-6-methoxy-1,2,3,4-tetrahydro-2-naphthylamine hydrochloride, 2.96 g of 2-(2-chloroethoxy)ethyl 3,4-dimethoxybenzoate, 1.54 g of sodium iodide, 1.07 g of anhydrous sodium carbonate and 30 ml of methyl ethyl ketone.

Elemental Analysis: Calcd. for $C_{26}H_{35}NO_6 \cdot HCl \cdot \frac{1}{2}H_2O$ (%): C, 62.08; H, 7.41; N, 2.78. Found (%): C, 62.44; H, 7.49; N, 3.00.

EXAMPLE 8

Using the procedures described in Example 3 (ii), 0.3 g of N-[4-(3,4-dimethoxybenzoyloxy)butyl]-6-methoxy-1,2,3,4-tetrahydro-2-naphthylamine hydrochloride was obtained as colorless plates having a melting point of 220°-222° C. (decomp.), starting from 1.1 g of 6-methoxy-1,2,3,4-tetrahydro-2-naphthylamine hydrochloride, 1.1 g of 4-chlorobutyl 3,4-dimethoxybenzoate, 1.0 g of sodium iodide, 1.0 g of anhydrous sodium carbonate and 30 ml of methyl ethyl ketone.

Elemental Analysis: Calcd. for $C_{24}H_{31}NO_5.HCl$ (%): C, 64.06; H, 7.17; N, 3.11. Found (%): C, 63.65; H, 7.06; N, 3.27.

EXAMPLE 9

(i) A mixture of 5.0 g of p-ethoxyphenyl acetic acid, 7.0 g of phosphoric pentachloride and 10 ml of anhydrous benzene was heated at 80° C. for 2 hours. The reaction solution was concentrated under reduced pressure and the residue obtained was dissolved in 20 ml of anhydrous dichloromethane. This solution was added dropwise to a mixture, cooled to −50° C., of 7.3 g of anhydrous aluminum chloride and 80 ml of anhydrous dichloromethane. Then, ethylene gas was fed into the solution for 20 minutes. Subsequently, the solution was stirred at room temperature (about 25° C.) for 4 hours. Into the reaction solution cooled with ice was added dropwise 30 ml of water. The dichloromethane layer was removed and washed with an 8% hydrochloric acid aqueous solution, water, a saturated sodium bicarbonate aqueous solution and water in this order. Then the dichloromethane layer was dried over anhydrous sodium sulfate and concentrated under reduced pressure to obtain 6-ethoxy-2-tetralone as a pale-yellow oily product. The crude product, 6-ethoxy-2-tetralone obtained as described above, was catalytically reduced in the presence of hydrogen in a mixture of 0.4 g of platinum oxide and 40 ml of a 20% ethylamine-ethanol solution. After take up of hydrogen had been completed, the platinum oxide catalyst was filtered from the reaction solution and the filtrate was concentrated under reduced pressure. Then the residue was extracted with chloroform and the chloroform layer as washed with a 2 N-NaOH aqueous solution and water in this order, dried over anhydrous sodium sulfate and concentrated under reduced pressure. Adding an ethanolic solution of hydrogen chloride having a concentration of about 18% to the residue, the solution was concentrated under reduced pressure to cause crystals to form. The crystals were recrystallized from a mixed solution of ethanol and diethyl ether to obtain 1.4 g of N-ethyl-6-ethoxy-1,2,3,4-tetrahydro-2 -naphthylamine hydrochloride as colorless needles having a melting point of 207°-209° C.

Elemental Analysis: Calcd. for $C_{14}H_{21}NO.HCl$ (%): C, 65.74; H, 8.67; N, 5.48. Found (%): C, 65.61; H, 8.70; N, 5.47.

(ii) Using the procedures as described in Example 3 (ii), 0.6 g of N-ethyl-N-[4-(3,4-dimethoxybenzoyloxy)butyl]-6-ethoxy-1,2,3,4-tetrahydro-2-naphthylamine hydrochloride was obtained as colorless crystals having a melting point of 129°-131° C., starting from 1.0 g of N-ethyl-6-ethoxy-1,2,3,4-tetrahydro-2-naphthylamine hydrochloride, 1.2 g of 4-chlorobutyl 3,4-dimethoxybenzoate, 1.0 g of sodium iodide, 1.0 g of anhydrous sodium carbonate and 40 ml of methyl ethyl ketone.

Elemental Analysis: Calcd. for $C_{27}H_{37}NO_5.HCl.\frac{1}{2}H_2O$ (%): C, 64.72; H, 7.85; N, 2.80. Found (%) C, 65.11; H, 7.59; N, 2.77.

EXAMPLE 10

(i) Using the procedures described in Example 9 (i), 1.1 g of N-ethyl-6-n-propoxy-1,2,3,4-tetrahydro-2-naphthylamine hydrochloride was obtained as colorless crystals having a melting point of 218.5°-219° C., starting from 5.0 g of p-n-propoxyphenyl acetic acid instead of p-ethoxyphenyl acetic acid.

Elemental Analysis: Calcd. for $C_{15}H_{23}NO.HCl$ (%): C, 66.77; H, 8.97; N, 5.19. Found (%): C, 66.81; H, 9.08; N, 5.24.

(ii) Using the procedures described in Example 3 (ii), 0.7 g of N-ethyl-N-[4-(3,4-dimethoxybenzoyloxy)butyl]-6-n-propoxy-1,2,3,4-tetrahydro-2-naphthylamine hydrochloride was obtained as colorless needles having a melting point of 112°-114° C., starting from 1.0 g of N-ethyl-6-n-propoxy-1,2,3,4-tetrahydro-2-naphthylamine hydrochloride, 1.2 g of 4-chlorobutyl 3,4-dimethoxybenzoate, 1.0 g of sodium iodide, 1.0 g of anhydrous sodium carbonate and 40 ml of methyl ethyl ketone.

Elemental Analysis: Calcd. for $C_{28}H_{39}NO_5.HCl.\frac{1}{2}H_2O$ (%): C, 65.29; H, 8.02; N, 2.72. Found (%): C, 65.35; H, 8.05, N, 2.66.

EXAMPLE 11

(i) Using the procedures described in Example 2 (i), 13.9 g of N-isopropyl-6-methoxy-1,2,3,4-tetrahydro-2-naphthylamine hydrochloride was obtained as colorless needles having a melting point of 184°-186° C., starting from 20 g of 6-methoxy-2-tetralone, 22 g of isopropylamine, 0.5 g of platinum oxide and 20 ml of absolute ethanol.

Elemental Analysis: Calcd. for $C_{14}H_{21}NO.HCl$ (%): C, 65.74; H, 8.67; N, 5.48 Found (%): C, 65.91; H, 8.72; N, 5.36.

EXAMPLE 12

(i) Using the procedures described in Example 2 (i), 25.0 g of N-n-propyl-6-methoxy-1,2,3,4-tetrahydro-2-naphthylamine hydrochloride was obtained as colorless crystals having a melting point of 247°-247.5° C. (decomp.), starting from 21.0 g of 6-methoxy-2-tetralone, 22 g of n-propylamine, 0.5 g of platinum oxide and 25 ml of absolute ethanol.

Elemental Analysis: Calcd. for $C_{14}H_{21}NO.HCl$ (%): C, 65.74; H, 8.67; N, 5.48. Found (%): C, 66.25, H, 8.63; N, 5.56.

(ii) Using the procedures described in Example 2 (ii), 2.35 g of N-n-propyl-N-[4-(3,4-dimethoxybenzoyloxy)butyl]-6-methoxy-1,2,3,4-tetrahydro-2-naphthylamine hydrochloride was obtained as a colorless oily product, starting from 2.0 g of N-n-propyl-6-methoxy-1,2,3,4-tetrahydro-2-naphthylamine hydrochloride, 3.15 g of 4-iodobutyl 3,4-dimethoxybenzoate, 1.9 g of anhydrous sodium carbonate and 50 ml of methyl ethyl ketone.

Elemental Analysis: Calcd. for $C_{27}H_{37}NO_5.HCl.\frac{1}{2}H_2O$ (%): C, 64.72; H, 7.85; N, 2.79. Found (%): C, 64.60; H, 8.09; N, 2.78.

EXAMPLE 13

Using the procedures described in Example 2 (ii), 1.9 g of N-methyl-N-[4-(3,4-dimethoxybenzoyloxy)butyl]-6-methoxy-1,2,3,4-tetrahydro-2-naphthylamine hydrochloride was obtained as a colorless oily product, starting from 2.0 g of N-methyl-6-methoxy-1,2,3,4-tetrahydro-2-naphthylamine hydrochloride, 3.3 g of 4-iodobutyl 3,4-dimethoxybenzoate, 2.1 g of anhydrous sodium carbonate and 50 ml of methyl ethyl ketone. Elemental Analysis: Calcd. for $C_{25}H_{33}NO_5.HCl.H_2O$ (%): C, 62.29; H, 7.53; N, 2.91. Found (%): C, 61.72; H, 7.08; N, 2.76.

EXAMPLE 14

Using 2.0 g of N-ethyl-6-methoxy-1,2,3,4-tetrahydro-2-naphthylamine hydrochloride, 3.3 g of 4-iodobutyl 3,4,5-trimethoxybenzoate, 0.9 g of anhydrous sodium carbonate and 40 ml of methyl ethyl ketone, the free base, N-ethyl-N-[4-(3,4,5-trimethoxybenzoyloxy)butyl]-6-methoxy-1,2,3,4-tetrahydro-2-naphthylamine, was obtained using the procedures described in Example 2 (ii). The free base was treated with methanesulfonic acid to obtain 1.5 g of N-ethyl-N-[4-(3,4,5-trimethoxybenzoyloxy)butyl]-6-methoxy-1,2,3,4-tetrahydro-2-naphthylamine methanesulfonate as a pale-yellow oil.

Elemental Analysis: Calcd. for $C_{27}H_{37}NO_6.CH_3SO_3H.2H_2O$ (%): C, 55.70; H, 7.51; N, 2.32. Found (%): C, 55.47; H, 7.25; N, 2.29.

EXAMPLE 15

Using the procedures described in Example 2 (ii), 2.9 g of N-ethyl-N-[2-(3,4-dimethoxybenzoyloxy)ethyl]-6-methoxy-1,2,3,4-tetrahydro-2-naphthylamine hydrochloride was obtained as colorless crystals having a melting point of 100°–101° C., starting from 2.5 g of N-ethyl-6-methoxy-1,2,3,4-tetrahydro-2-naphthylamine hydrochloride, 3.6 g of 2-iodoethyl 3,4-dimethoxybenzoate, 1.2 g of anhydrous sodium carbonate and 40 ml of methyl ethyl ketone.

Elemental Analysis: Calcd. for $C_{24}H_{31}NO_5.HCl.\frac{1}{2}H_2O$ (%): C, 62.80; H, 7.25; N, 3.05. Found (%): C, 62.41; H, 6.84; N, 3.14.

EXAMPLE 16

Using the procedures described in Example 2 (ii), 2.4 g of N-ethyl-N-[3-(3,4-dimethoxybenzoyloxy)propyl]-6-methoxy-1,2,3,4-tetrahydro-2-naphthylamine hydrochloride was obtained as colorless crystals having a melting point of 146°–148° C., starting from 2.0 g of N-ethyl-6-methoxy-1,2,3,4-tetrahydro-2-naphthylamine hydrochloride, 3.4 g of 3-iodopropyl 3,4-dimethoxybenzoate, 1.2 g of anhydrous sodium carbonate and 60 ml of methyl ethyl ketone.

Elemental Analysis: Calcd. for $C_{25}H_{33}NO_5.HCl$ (%): C, 64.71; H, 7.39; N, 3.02. Found (%): C, 64.55; H, 7.44; N, 2.84.

EXAMPLE 17

Using the procedures described in Example 3 (ii), 1.34 g of N-ethyl-N-[4-(4-methoxybenzoyloxy)butyl]-6-methoxy-1,2,3,4-tetrahydro-2-naphthylamine hydrochloride was obtained as colorless crystals having a melting point of 120°–121° C., starting from 2.1 g of N-ethyl-6-methoxy-1,2,3,4-tetrahydro-2-naphthylamine hydrochloride, 3.2 g of 4-chlorobutyl p-methoxybenzoate, 3.0 g of sodium iodide, 3.0 g of anhydrous sodium carbonate and 60 ml of methyl ethyl ketone.

Elemental Analysis: Calcd. for $C_{25}H_{33}NO_4.HCl$ (%): C, 66.96; H, 7.65; N, 3.13. Found (%): C, 67.32; H, 7.74; N, 3.20.

EXAMPLE 18

Using the procedures described in Example 3 (ii), 0.8 g of N-ethyl-N-[4-(3,4-dimethoxybenzoyloxy)butyl]-5,8-dimethoxy-1,2,3,4-tetrahydro-2-naphthylamine hydrochloride was obtained as an oily product, starting from 1.3 g of N-ethyl-5,8-dimethoxy-1,2,3,4-tetrahydro-2-naphthylamine hydrochloride, 1.8 g of 4-chlorobutyl 3,4-dimethoxybenzoate, 0.9 g of sodium iodide, 0.8 g of anhydrous sodium carbonate and 80 ml of methyl ethyl ketone.

Elemental Analysis: Calcd. for $C_{27}H_{37}NO_6.HCl.H_2O$ (%): C, 61.64; H, 7.66; N, 2.66. Found (%): C, 61.58; H, 7.24; N, 2.59.

REFERENCE EXAMPLE 1

The starting material used in Example 18, N-ethyl-5,8-dimethoxy-1,2,3,4-tetrahydro-2-naphthylamine hydrochloride, can be obtained using the following method.

A mixture of 0.7 g of 5,8-dimethoxy-1-hydroxy-1,2,3,4-tetrahydro-2-naphthylamine, 0.3 g of 15% palladium on carbon, 0.5 ml of 70% perchloric acid aqueous solution and 30 ml of acetic acid was catalytically reduced under irradiation with light from an incandescent lamp. After the theoretical amount of hydrogen had been absorbed, the palladium carbon catalyst was filtered off and to the filtrate was added 0.5 g of potassium acetate. The solution was stirred and insoluble materials were removed by filtration. The filtrate was concentrated under reduced pressure to obtain 0.7 g of a red-brown resinous residue. After 10 ml of acetic acid and 2 ml of acetic anhydride were added to the residue, the solution was heated at 60° C. for 2 hours in a water bath, followed by concentration under reduced pressure and extraction with dichloromethane. The dichloromethane layer was washed with water, dried and concentrated under reduced pressure to obtain a residue. The residue was recrystallized from acetone-diethyl ether to obtain 0.3 g of N-acetyl-5,8-dimethoxy-1,2,3,4-tetrahydro-2-naphthylamine having a melting point of 156°–158° C.

Elemental Analysis: Calcd. for $C_{14}H_{19}NO_3$ (%): C, 67.44; N, 7.68; N, 5.62. Found (%): C, 67.69; H, 7.71; N, 5.40.

After 1.0 g of lithium aluminum hydride was suspended in 20 ml of tetrahydrofuran, 2.0 g of N-acetyl-5,8-dimethoxy-1,2,3,4-tetrahydro-2-naphthylamine, produced as described above, dissolved in 7 ml of tetrahydrofuran was added dropwise into the suspension. After the addition, the solution was heated for 2.5 hours at reflux. After cooling the reaction solution with an ice-bath, a mixed solution of 1 ml of water and 10 ml of tetrahydrofuran was added dropwise to the reaction solution. Then, 1 ml of a 15%-NaOH aqueous solution and 3 ml of water were added dropwise thereto in this order. Then, insoluble material was filtered off from the reaction solution and the filtrate was concentrated under reduced pressure and extracted with chloroform. The chloroform layer was washed with water and concentrated under reduced pressure. An ethanolic solution of hydrogen chloride having a concentration of about 18% was added to the residue and the solution obtained was concentrated under reduced pressure. Subsequently, by adding acetone to the concentrated solution, crystals were obtained. On recrystallization from ethanol-diethyl ether, 1.3 g of N-ethyl-5,8-dimethoxy-1,2,3,4-tetrahydro-2-naphthylamine hydrochloride was obtained having a melting point of 240°–242° C.

EXAMPLE 19

Using the procedures described in Example 3 (ii), 2.2 g of N-ethyl-N-[4-(3,4-dimethoxybenzoyloxy)butyl]-5-methoxy-1,2,3,4-tetrahydro-2-naphthylamine hydrochloride was obtained as colorless crystals having a melting point of 162°–164° C., starting from 2.1 g of N-ethyl-5-methoxy-1,2,3,4-tetrahydro-2-naphthylamine hydrochloride, 3.2 g of 4-chlorobutyl 3,4-dimethoxybenzoate, 3.0 g of sodium iodide, 3.0 g of anhydrous sodium carbonate and 90 ml of methyl ethyl ketone.

Elemental Analysis:
Calcd. for $C_{26}H_{35}NO_5 \cdot HCl$ (%): C, 65.33; H, 7.59; N, 2.93. Found (%): C, 65.32; H, 7.87; N, 2.78.

EXAMPLE 20

Using the procedures described in Example 3 (ii), 1.5 g of N-ethyl-N-[4-(3,4-dimethoxybenzoyloxy)butyl]-8-methoxy-1,2,3,4-tetrahydro-2-naphthylamine hydrochloride was obtained as colorless crystals having a melting point of 133°–135° C., starting from 2.4 g of N-ethyl-8-methoxy-1,2,3,4-tetrahydro-2-naphthylamine hydrochloride, 3.7 g of 4-chlorobutyl 3,4-dimethoxybenzoate, 3.7 g of sodium iodide, 3.7 g of anhydrous sodium carbonate and 100 ml of methyl ethyl ketone.

Elemental Analysis: Calcd. for $C_{26}H_{35}NO_5 \cdot HCl$ (%): C, 65.33; H, 7.59; N, 2.83. Found (%): C, 65.10; H, 8.06; N, 2.99.

EXAMPLE 21

Using the procedures described in Example 3 (ii), 4.8 g of N-ethyl-N-[6-(3,4-dimethoxybenzoyloxy)hexyl]-8-methoxy-1,2,3,4-tetrahydro-2-naphthylamine hydrochloride was obtained as a pale-yellow oily product, starting from 3.5 g of N-ethyl-8-methoxy-1,2,3,4-tetrahydro-2-naphthylamine, 6.2 g of 6-chlorohexyl 3,4-dimethoxybenzoate, 3.1 g of sodium iodide, 2.2 g of anhydrous sodium carbonate and 100 ml of methyl ethyl ketone.

Elemental Analysis: Calcd. for $C_{28}H_{39}NO_5 \cdot HCl \cdot H_2O$ (%): C, 64.17; H, 8.08; N, 2.67. Found (%): C, 64.65; H, 7.93; N, 2.59.

EXAMPLE 22

(i) Using the procedures described in Example 2 (i), 10.7 g of N-ethyl-7-methoxy-1,2,3,4-tetrahydro-2-naphthylamine hydrochloride was obtained as colorless crystals having a melting point of 217°–219° C., starting from 12.4 g of 7-methoxy-2-tetralone, 60 ml of a 19% ethylamine-ethanol solution and 0.4 g of platinum oxide.

Elemental Analysis: Calcd. for $C_{13}H_{19}NO \cdot HCl$ (%): C, 64.58; H, 8.34; N, 5.79 Found (%): C, 64.23; H, 8.11; N, 5.70.

(ii) Using the procedures described in Example 2 (ii), 2.1 g of N-ethyl-N-[4-(3,4-dimethoxybenzoyloxy)butyl]-7-methoxy-1,2,3,4-tetrahydro-2-naphthylamine hydrochloride was obtained as colorless crystals having a melting point of 160°–161° C., starting from 2.0 g of N-ethyl-7-methoxy-1,2,3,4-tetrahydro-2-naphthylamine hydrochloride, 3.2 g of 4-iodobutyl 3,4-dimethoxybenzoate, 3.0 g of anhydrous sodium carbonate and 50 ml of methyl ethyl ketone.

Elemental Analysis: Calcd. for $C_{26}H_{35}NO_5 \cdot HCl$ (%): C, 65.33; H, 7.59; N, 2.93. Found (%): C, 64.96; H, 7.66; N, 3.09.

EXAMPLE 23

(i) Using the procedures described in Example 2 (i) 7.2 g of N-ethyl-6,7-methylenedioxy-1,2,3,4-tetrahydro-2-naphthylamine hydrochloride was obtained as colorless needles having a melting point of 269.5°–271° C., starting from 17.0 g of 6,7-methylenedioxy-2-tetralone, 120 ml of a 19% ethylamine-ethanol solution, 0.4 g of platinum oxide and 100 ml of absolute ethanol.

Elemental Analysis: Calcd. for $C_{13}H_{17}NO_2 \cdot HCl$ (%): C, 61.05; H, 7.09; N, 5.48. Found (%): C, 61.66; H, 7.14; N, 5.51.

(ii) Using the procedures as described in Example 3 (ii), 1.2 g of N-ethyl-N-[4-(3,4-dimethoxybenzoyloxy)butyl]-6,7-methylenedioxy-1,2,3,4-tetrahydro-2-naphthylamine hydrocholride was obtained as colorless needles having a melting point of 151.5°–153° C., starting from 2.0 g of N-ethyl-6,7-methylenedioxy-1,2,3,4-tetrahydro-2-naphthylamine hydrochloride, 3.3 g of 4-chlorobutyl 3,4-dimethoxybenzoate, 3.0 g of sodium iodide, 3.0 g of anhydrous sodium carbonate and 40 ml of methyl ethyl ketone.

Elemental Analysis: Calcd. for $C_{26}H_{33}NO_6 \cdot HCl$ (%): C, 63.47; H, 6.97; N, 2.84. Found (%): C, 63.77; H, 6.91; N, 2.78.

EXAMPLE 24

(i) To a mixture of 8.8 g of N-ethyl-6-methoxy-1,2,3,4-tetrahydro-2-naphthylamine, 6.1 g of triethylamine and 80 ml of anhydrous benzene, 7.1 g of 3-(methoxycarbonyl)-propionyl chloride dissolved in 10 ml of anhydrous benzene was added dropwise. After the resulting solution was heated for 2.5 hours at reflux, the solution was allowed to stand overnight at room temperature (about 25° C.). The reaction solution was washed with a 2N-HCl aqueous solution, water, a 2 N-NaOH aqueous solution and water in order, and dried over anhydrous sodium sulfate. Then, the solution was concentrated under reduced pressure to obtain 12.5 g of N-ethyl-N-[3-(methoxycarbonyl)propionyl]-6-methoxy-1,2,3,4-tetrahydro-2-naphthylamine as a pale-yellow oily product.

(ii) To a suspension of 8.3 g of lithium aluminum hydride and 200 ml of anhydrous tetrahydrofuran, a solution of 14.5 g of N-ethyl-N-[3-(methoxycarbonyl)-propionyl]-6-methoxy-1,2,3,4-tetrahydro-2-naphthylamine in 100 ml of anhydrous tetrahydrofuran was added dropwise. After heating the resulting solution for 4.5 hours at reflux, a mixed solution of 8.3 ml of water and 50 ml of tetrahydrofuran as added dropwise to the solution under cooling with ice. Then, 8.3 ml of a 15% sodium hydroxide aqueous solution was added dropwise to the resulting solution and lastly 25 ml of water was added dropwise thereto to precipitate insoluble materials. After removing the insoluble materials by filtration, the filtrate was concentrated under reduced pressure to obtain a residue. After the residue was extracted with benzene, the benzene layer was washed with water, dried over anhydrous sodium sulfate and concentrated under reduced pressure to obtain 10.8 g of N-ethyl-N-(4-hydroxybutyl)-6-methoxy-1,2,3,4-tetrahydro-2-naphthylamine as a colorless oily product. This product was treated with an ethanolic solution of hydrogen chloride having a concentration of about 18% to obtain N-ethyl-N-(4-hydroxybutyl)-6-methoxy-1,2,3,4-tetrahydro-2-naphthylamine hydrochloride as colorless crystals having a melting point of 124°–126° C.

Elemental Analysis: Calcd. for $C_{17}H_{27}NO_2 \cdot HCl$ (%): C, 65.05; H, 8.99; N, 4.46. Found (%): C, 65.10; H, 8.91; N, 4.77.

(iii) 2.9 g of 3,4-dimethoxybenzoic acid and 4 ml of thionyl chloride were heated for 4 hours at reflux and concentrated under reduced pressure to obtain 3,4-dimethoxybenzoyl chloride. The 3,4-dimethoxybenzoyl chloride was dissolved in 10 ml of anhydrous benzene, and the resulting solution was added dropwise to a solution of 4.0 g of N-ethyl-N-(4-hydroxybutyl)-6-methoxy-1,2,3,4-tetrahydro-2-naphthylamine and 2.2 g of triethylamine in 50 ml of anhydrous benzene. After the addition, the resulting solution was stirred for 30 minutes at room temperature (about 25° C.) and heated for 3.5 hours at reflux. The reaction solution was washed with water, a 2 N-NaOH aqueous solution and water in this order, dried over anhydrous sodium sulfate and concentrated under reduced pressure. The residue obtained was purified through silica gel chromatography to obtain N-ethyl-N-[4-(3,4-dimethoxybenzoyloxy)butyl]-6-methoxy-1,2,3,4-tetrahydro-2-naphthylamine as a colorless oily product. To this oily product was added an ethanolic solution of hydrogen chloride having a concentration of about 18% and the resulting solution was concentrated under reduced pressure to obtain a residue. The residue was dissolved in a mixed solvent of acetone and diethyl ether, and the solution was left at a temperature of about 2° to 3° C. to form crystals. By collecting the crystals through filtration and recrystallization from a mixed solvent of acetone and diethyl ether, 3.0 g of N-ethyl-N-[4-(3,4-dimethoxybenzoyloxy)butyl]-6-methoxy-1,2,3,4-tetrahydro-2-naphthylamine hydrochloride was obtained as colorless crystals having a melting point of 139°–140° C. The melting point, the infrared spectra and other physical data of this product corresponded to the date of the compound obtained in Example 2 (ii).

EXAMPLE 25

(i) Using the procedures described in Example 24 (i), 10.8 g of N-ethyl-N-[5-ethoxycarbonyl)pentanoyl]-6-methoxy-1,2,3,4-tetrahydro-2-naphthylamine was obtained as a colorless oily product, starting from the free base, N-ethyl-6-methoxy-1,2,3,4-tetrahydro-2-naphthylamine, obtained in a conventional manner from 7.5 g of the hydrochloride-addition salt thereof and 6.7 g of 5-(ethoxycarbonyl)-pentanoyl chloride.

(ii) Using the procedures described in Example 24 (ii), 8.2 g of N-ethyl-N-(6-hydroxyhexyl)-6-methoxy-1,2,3,4-tetrahydro-2-naphthylamine as obtained as a pale-yellow oily product, starting from 10.8 g of N-ethyl-N-[5-(ethoxycarbonyl)-pentanoyl]-6-methoxy-1,2,3,4-tetrahydro-2-naphthylamine and 4.5 g of lithium aluminum hydride.

(iii) Using the procedures described in Example 24 (iii), 7.3 g of N-ethyl-N-[6-(3,4-dimethoxybenzoyloxy)hexyl]-6-methoxy-1,2,3,4-tetrahydro-2-naphthylamine hydrochloride was obtained as colorless crystals having a melting point of 119°–120° C., starting from 3,4-dimethoxybenzoyl chloride obtained from 5.2 g of 3,4-dimethoxybenzoic acid and 8.2 g of N-ethyl-N-(6-hydroxyhexyl)-6-methoxy-1,2,3,4-tetrahydro-2-naphthylamine. The melting point and infrared spectra of this product corresponded to those of the compound obtained in Example 3 (ii).

EXAMPLE 26

(i) Using the procedures described in Example 24 (i), 4.6 g of N-ethyl-N-[7-(ethoxycarbonyl)heptanoyl]-6-methoxy-1,2,3,4-tetrahydro-2-naphthylamine was obtained as a red-brown oily product, starting from 3 g of N-ethyl-6-methoxy-1,2,3,4-tetrahydro-2-naphthylamine hydrochloride and 2.9 g of 7-(ethoxycarbonyl)heptanoyl chloride.

(ii) Using the procedures described in Example 24 (ii), 3.4 g of N-ethyl-N-(8-hydroxyoctyl)-6-methoxy-1,2,3,4-tetrahydro-2-naphthylamine was obtained as a colorless oily product, starting from 4.6 g of N-ethyl-N-[7-(ethoxycarbonyl)heptanoyl]-6-methoxy-1,2,3,4-tetrahydro-2-naphthylamine and 2.0 g of lithium aluminum hydride.

(iii) Using the procedures described in Example 24 (iii), 3.5 g of N-ethyl-N-[8-(3,4-dimethoxybenzoyloxy)octyl]-6-methoxy-1,2,3,4-tetrahydro-2-naphthylamine hydrochloride was obtained as a pale-yellow oily product, starting from 3.4 g of N-ethyl-N-(8-hydroxyoctyl)-6-methoxy-1,2,3,4-tetrahydro-2-naphthylamine and 2.05 g of 3,4-dimethoxybenzoic acid.

Elemental Analysis: Calcd. for $C_{30}H_{43}NO_5 \cdot HCl \cdot \frac{1}{2}H_2O$ (%): C, 66.34; H, 8.35; N, 2.58. Found (%): C, 66.52; H, 8.18; N, 2.44.

EXAMPLE 27

(i) Using the procedures described in Example 24 (i), 11.4 g of N-ethyl-N-[9-(ethoxycarbonyl)nonanoyl]-6-methoxy-1,2,3,4-tetrahydro-2-naphthylamine was obtained as a pale-yellow oily product, starting from 6.11 g of N-ethyl-6-methoxy-1,2,3,4-tetrahydro-2-naphthylamine hydrochloride and 7.1 g of 9-(ethoxycarbonyl)nonanoyl chloride.

(ii) Using the procedures described in Example 24 (ii), 9.3 g of N-ethyl-N-(10-hydroxydecyl)-6-methoxy-1,2,3,4-tetrahydro-2-naphthylamine was obtained as an oily product, starting from 11.4 g of N-ethyl-N-[9-(ethoxycarbonyl)nonanoyl]-6-methoxy-1,2,3,4-tetrahydro-2-naphthylamine and 5.2 g of lithium aluminum hydride.

(iii) Using the procedures described in Example 24 (iii), 8.8 g of N-ethyl-N-[10-(3,4-dimethoxybenzoyloxy)decyl]-6-methoxy-1,2,3,4-tetrahydro-2-naphthylamine hydrochloride was obtained as an oily product, starting from 9.3 g of N-ethyl-N-(10-hydroxydecyl)-6-methoxy-1,2,3,4-tetrahydro-2-naphthylamine and 5.17 g of 3,4-dimethoxybenzoic acid.

Elemental Analysis: Calcd. for $C_{32}H_{47}NO_5 \cdot HCl \cdot \frac{1}{2}H_2O$ (%): C, 67.42; H, 8.60; N, 2.46. Found (%): C, 67.24; H, 8.86; N, 2.41.

EXAMPLE 28

(i) Using the procedures described in Example 24 (i), 0.68 g of N-ethyl-N-[2-(ethoxycarbonyl)-2-methylpropionyl]-6-methoxy-1,2,3,4-tetrahydro-2-naphthylamine was obtained as an oily product, starting from 0.6 g of N-ethyl-6-methoxy-1,2,3,4-tetrahydro-2-naphthylamine hydrochloride and 0.5 g of 2-(ethoxycarbonyl)-2-methylpropionyl chloride.

(ii) Using the procedures described in Example 24 (ii), 0.5 g of N-ethyl-N-(3-hydroxy-2,2-dimethylpropyl)-6-methoxy-1,2,3,4-tetrahydro-2-naphthylamine was obtained as a colorless oily product, starting from 0.66 g of N-ethyl-N-[2-(ethoxycarbonyl)-2-methylpropionyl]-6-methoxy-1,2,3,4-tetrahydro-2-naphthylamine and 0.55 g of lithium aluminum hydride.

(iii) Using the procedures described in Example 24 (iii), 0.2 g of N-ethyl-N-[3-(3,4-dimethoxybenzoyloxy)-2,2-dimethylpropyl]-6-methoxy-1,2,3,4-tetrahydro-2-naphthylamine hydrochloride was obtained as colorless crystals having a melting point of 165°–168° C., starting from 0.45 g of N-ethyl-N-(3-hydroxy-2,2-dimethylpropyl)-6-methoxy-1,2,3,4-tetrahydro-2-naphthylamine and 0.3 g of 3,4-dimethoxybenzoic acid.

Elemental Analysis: Calcd. for $C_{27}H_{37}NO_5.HCl$ (%): C, 65.90; H, 7.78; N, 2.85. Found (%): C, 65.36; H, 7.77; N, 2.98.

EXAMPLE 29

(i) Using the procedures described in Example 24 (i), 17.5 g of N-isopropyl-N-[3-(methoxycarbonyl)propionyl]-6-methoxy-1,2,3,4-tetrahydro-2-naphthylamine was obtained as an oil product, starting from 13.8 g of N-isopropyl-6-mwethoxy-1,2,3,4-tetrahydro-2-naphthylamine hydrochloride and 9.1 g of 3-(methoxycarbonyl)propionyl chloride.

(ii) Using the procedures described in Example 24 (ii), 12.85 g of N-isopropyl-N-(4-hydroxybutyl)-6-methoxy-1,2,3,4-tetrahydro-2-naphthylamine was obtained as an oily product, starting from 17.5 g of N-isopropyl-N-[3-(methoxycarbonyl)propionyl]-6-methoxy-1,2,3,4-tetrahydro-2-naphthylamine and 7.2 g of lithium aluminum hydride.

(iii) Using the procedures described in Example 24 (iii), 16.2 g of N-isopropyl-N-[4-(3,4-dimethoxybenzoyloxy)butyl]-6-methoxy-1,2,3,4-tetrahydro-2-naphthylamine hydrochloride was obtained as colorless needles having a melting point of 172°–174° C., starting from 12.85 g of N-isopropyl-N-(4-hydroxybutyl)-6-methoxy-1,2,3,4-tetrahydro-2-naphthylamine and 8.12 g of 3,4-dimethoxybenzoic acid. The melting point and IR-spectra of this product corresponded to those of the compound obtained in Example 11 (ii).

EXAMPLE 30

(i) Using the procedures described in Example 24 (i), 19.8 g of N-n-propyl-N-[3-(methoxycarbonyl)propionyl]-6-methoxy-1,2,3,4-tetrahydro-2-naphthylamine was obtained as an oily product, starting from 15 g of N-n-propyl-6-methoxy-1,2,3,4-tetrahydro-2-naphthylamine hydrochloride and 9.7 g of 3-(methoxycarbonyl)propionyl chloride.

(ii) Using the procedures described in Example 24 (ii), 13.5 of N-n-propyl-N-(4-hydroxybutyl)-6-methoxy-1,2,3,4-tetrahydro-2-naphthylamine was obtained as an oily product, starting from 19.8 g of N-n-propyl-N-[3-(methoxycarbonyl)-propionyl]-6-methoxy-1,2,3,4-tetrahydro-2-naphthylamine and 10 g of lithium aluminum hydride.

(iii) Using the procedures described in Example 24 (iii), 19.0 g of N-n-propyl-N-[4-(3,4-dimethoxybenzoyloxy)butyl]-6-methoxy-1,2,3,4-tetrahydro-2-naphthylamine hydrochloride was obtained as a colorless resinous product, starting from 13.45 g of N-n-propyl-N-(4-hydroxybutyl)-6-methoxy-1,2,3,4-tetrahydro-2-naphthylamine and 8.5 g of 3,4-dimethoxybenzoic acid. The IR-spectra of this product corresponded to that of the compound obtained in Example 12 (ii).

EXAMPLE 31

(i) A mixture of 5.3 g of 6-methoxy-2-tetralone, 3 g of cyclohexylamine and 70 ml of absolute ethanol was heated for 7 hours at reflux. To the mixture was added 0.3 g of platinum oxide, and a catalytic reduction was conducted in the presence of hydrogen. After absorption of hydrogen gas was completed, the platinum oxide catalyst in the reaction solution was removed by filtration and the filtrate was concentrated under reduced pressure to obtain a residue. Then, an ethanol solution saturated with hydrogen chloride was added to the residue and the solution was concentrated under reduced pressure. The residue obtained was dissolved in acetone and the solution was stirred to form crystals. After collecting the crystals by filtration and recrystallizing from a mixed solvent of ethanol and diethyl ether, 5.0 g of N-cyclohexyl-6-methoxy-1,2,3,4-tetrahydro-2-naphthylamine hydrochloride was obtained as colorless needles having a melting point of 252°–254° C.

Elemental Analysis: Calcd. for $C_{17}H_{25}NO.HCl$ (%): C, 69.01; H, 8.86; N, 4.73. Found (%); C, 69.33; H, 8.90; N, 4.64.

(ii) Using the procedures described in Example 24 (i), 5.5 g of N-cyclohexyl-N-[3-(methoxycarbonyl)propionyl]-6-methoxy-1,2,3,4-tetrahydro-2-naphthylamine was obtained as a red-brown oily product, starting from 5.0 g of N-cyclohexyl-6-methoxy-1,2,3,4-tetrahydro-2-naphthylamine hydrochloride and 2.8 g of 3-(methoxycarbonyl)propionyl chloride.

(iii) Using the procedures described in Example 24 (ii), 1.45 g of N-cyclohexyl-N-(4-hydroxybutyl)-6-methoxy-1,2,3,4-tetrahydro-2-naphthylamine was obtained as a yellow oily product, starting from 1.87 g of N-cyclohexyl-N-[3-(methoxycarbonyl)propionyl]-6-methoxy-1,2,3,4-tetrahydro-2-naphthylamine and 0.95 g of lithium aluminum hydride.

(iv) Using the procedures described in Example 24 (iii), 2.6 g of N-cyclohexyl-N-[4-(3,4-dimethoxybenzoyloxy)butyl]-6-methoxy-1,2,3,4-tetrahydro-2-naphthylamine hydrochloride was obtained as a pale-yellow oily product, starting from 2.8 g of N-cyclohexyl-N-(4-hydroxybutyl)-6-methoxy-1,2,3,4-tetrahydro-2-naphthylamine and 2.0 g of 3,4-dimethoxybenzoic acid.

Elemental Analysis:
Calcd. for $C_{30}H_{41}NO_5.HCl.\frac{1}{2}H_2O$ (%): C, 66.59; H, 8.01; N, 2.59. Found (%): C, 66.58; H, 7.78; N, 2.54.

EXAMPLE 32

Using the procedures described in Example 24 (iii), 0.07 g of N-ethyl-N-(4-benzoyloxybutyl)-6-methoxy-1,2,3,4-tetrahydro-2-naphthylamine hydrochloride was obtained as colorless crystals having a melting point of 114°–116° C., starting from 0.2 g of N-ethyl-N-(4-hydroxybutyl)-6-methoxy-1,2,3,4-tetrahydro-2-naphthylamine and 0.16 g of benzoyl chloride.

Elemental Analysis: Calcd. for $C_{24}H_{31}NO_3.HCl$ (%): C, 68.97; H, 7.72; N, 3.35. Found (%): C, 68.74; H, 7.70; N, 3.46.

EXAMPLE 33

Using the procedures described in Example 24 (iii), 0.82 g of N-ethyl-N-[4-(3,4-methylenedioxybenzoyloxy)butyl]-6-methoxy-1,2,3,4-tetrahydro-2-naphthylamine hydrochloride was obtained as colorless crystals having a melting point of 118°–120° C., starting from 1.4 g of N-ethyl-N-(4-hydroxybutyl)-6-methoxy-1,2,3,4-tetrahydro-2-naphthylamine and 1.0 g of piperonylic acid.

Elemental Analysis: Calcd. for $C_{25}H_{31}NO_5.HCl$ (%): C, 64.99; H, 6.98; N, 3.03. Found (%): C. 64.98; H, 7.02; N, 3.54.

EXAMPLE 34

Using the procedures described in Example 24 (iii), 0.55 g of N-ethyl-N-[4-(2,6-dimethoxybenzoyloxy)-butyl]-6-methoxy-1,2,3,4-tetrahydro-2-naphthylamine hydrochloride was obtained as an oily product, starting from 1.5 g of N-ethyl-N-(4-hydroxybutyl)-6-methoxy-1,2,3,4-tetrahydro-2-naphthylamine and 1.0 g of 2,6-dimethoxybenzoic acid.

Elemental Analysis: Calcd. for $C_{26}H_{35}NO_5.HC1.\frac{1}{2}H_2O$ (%): C, 64.12; H, 7.66; N, 2.88. Found (%): C, 64.01; H, 7.75; N, 3.08.

EXAMPLE 35

Using the procedures described in Example 24 (iii), 0.18 g of N-ethyl-N-[4-(4-ethoxybenzoyloxy)butyl]-6-methoxy-1,2,3,4-tetrahydro-2-naphthylamine hydrochloride was obtained as colorless crystals having a melting point of 119°–120° C., starting from 0.2 g of N-ethyl-N-(4-hydroxybutyl)-6-methoxy-1,2,3,4-tetrahydro-2-naphthylamine and 0.132 g of p-ethoxybenzoic acid.

Elemental Analysis: Calcd. for $C_{26}H_{35}NO_4.HCl$ (%): C, 67.59; H, 7.85; N, 3.03. Found (%): C, 67.38; H, 7.86; N, 3.16.

EXAMPLE 36

Using the procedures described in Example 24 (iii), 0.23 g of N-ethyl-N-[4-(4-n-propoxybenzoyloxy)butyl]-6-methoxy-1,2,3,4-tetrahydro-2-naphthylamine hydrochloride was obtained as colorless crystals having a melting point of 123°–124° C., starting from 0.2 g of N-ethyl-N-(4-hydroxybutyl)-6-methoxy-1,2,3,4-tetrahydro-2-naphthylamine and 0.15 g of p-n-propoxybenzoic acid.

Elemental Analysis: Calcd. for $C_{27}H_{37}NO_4.HCl$ (%): C, 68.12; H, 8.05; N, 2.94. Found (%): C, 68.19; H, 8.06; N, 3.13.

EXAMPLE 37

Using the procedures described in Example 24 (iii), 0.2 g of N-ethyl-N-[4-(3,4,5-triethoxybenzoyloxy)butyl]-6-methoxy-1,2,3,4-tetrahydro-2-naphthylamine hydrochloride was obtained as an oily product, starting from 0.2 g of N-ethyl-N-(4-hydroxybutyl)-6-methoxy-1,2,3,4-tetrahydro-2-naphthylamine and 0.2 g of 3,4,5-triethoxybenzoic acid.

Elemental Analysis: Calcd. for $C_{30}H_{43}NO_6.HCl$ (%): C, 65.50; H, 8.06; N, 2.55. Found (%): C, 65.37; H, 8.00; N, 2.25.

EXAMPLE 38

Using the procedures described in Example 24 (iii), 0.2 g of N-ethyl-N-[4-(3-methoxy-4-ethoxybenzoyloxy)butyl]-6-methoxy-1,2,3,4-tetrahydro-2-naphthylamine hydrochloride was obtained as a colorless oily product, starting from 0.28 g of N-ethyl-N-(4-hydroxybutyl)-6-methoxy-1,2,3,4-tetrahydro-2-naphthylamine and 0.22 g of 3-methoxy-4-ethoxybenzoic acid.

Elemental Analysis: Calcd. for $C_{27}H_{37}NO_5.HCl.\frac{1}{2}H_2O$ (%): C, 64.72; H, 7.85; N, 2.79. Found (%): C, 64.50; H, 7.91; N, 2.56.

EXAMPLE 39

Using the procedures described in Example 24 (iii), 0.85 g of N-ethyl-N-[4-(3-methoxybenzoyloxy)butyl]-6-methoxy-1,2,3,4-tetrahydro-2-naphthylamine hydrochloride was obtained as a colorless powder having a melting point of 139°–140° C., starting from 0.9 g of m-methoxybenzoic acid and 1.5 g of N-ethyl-N-(4-hydroxybutyl)-6-methoxy-1,2,3,4-tetrahydro-2-naphthylamine.

Elemental Analysis: Calcd. for $C_{25}H_{33}NO_4.HCl$ (%): C, 67.02; H, 7.65; N, 3.13. Found (%): C, 67.09; H, 7.57; N, 3.11.

EXAMPLE 40

Using the procedures described in Example 24 (iii), 1.15 g of N-ethyl-N-[4-(4-methylbenzoyloxy)butyl]-6-methoxy-1,2,3,4-tetrahydro-2-naphthylamine hydrochloride was obtained as a colorless powder having a melting point of 138°–140° C., starting from 0.8 g of p-toluic acid and 1.5 g of N-ethyl-N-(4-hydroxybutyl)-6-methoxy-1,2,3,4-tetrahydro-2-naphthylamine.

Elemental Analysis: Calcd. for $C_{25}H_{33}NO_3.HCl$ (%): C, 69.51; H, 7.93; N, 3.24. Found (%): C, 69.85; H, 7.91; N, 3.09.

EXAMPLE 41

Using the procedures described in Example 24 (iii), 1.5 g of N-ethyl-N-[4-(3,4-dichlorobenzoyloxy)butyl]-6-methoxy-1,2,3,4-tetrahydro-2-naphthylamine hydrochloride was obtained as colorless needles having a melting point of 117°–118° C., starting from 2.0 g of N-ethyl-N-(4-hydroxybutyl)-6-methoxy-1,2,3,4-tetrahydro-2-naphthylamine and 1.7 g of 3,4-dichlorobenzoyl chloride.

Elemental Analysis: Calcd. for $C_{24}H_{29}Cl_2NO_3.HCl$ (%): C, 59.20; H, 6.21; N, 2.88. Found (%): C, 59.17; H, 6.26; N, 2.87.

EXAMPLE 42

Using the procedures described in Example 24 (iii), 3.0 g of N-ethyl-N-{4-[3,4-bis(benzyloxy) benzoyloxy]-butyl}-6-methoxy-1,2,3,4-tetrahydro-2-naphthylamine hydrochloride was obtained as a colorless powder having a melting point of 139°–140° C., starting from 2.0 g of N-ethyl-N-(4-hydroxybutyl)-6-methoxy-1,2,3,4-tetrahydro-2-naphthylamine and 2.5 g of 3,4-bis(benzyloxy)benzoic acid.

Elemental Analysis: Calcd. for $C_{38}H_{43}NO_5.HCl$ (%): C, 72.42; H, 7.04; N, 2.22 Found (%): C, 72.66; H, 7.13; N, 2.37.

2.5 g of N-ethyl-N-{4-[3,4-bis(benzyloxy)benzoyloxy]-butyl}-6-methoxy-1,2,3,4-tetrahydro-2-naphthylamine hydrochloride, 70 ml of water, 70 ml of ethanol and 0.5 g of a 5% palladium on carbon were mixed and reduced catalytically at a usual temperature under usual pressure. After absorption of the theoretical amount of hydrogen, the palladium on carbon catalyst was removed by filtration. The filtrate was concentrated under reduced pressure to obtain 1.5 g of N-ethyl-N-[4-(3,4-dihydroxybenzoyloxy)butyl]-6-methoxy-1,2,3,4-tetrahydro-2-naphthylamine hydrochloride as a colorless resinous material.

Elemental Analysis: Calcd. for $C_{24}H_{31}NO_5.HCl.H_2O$ (%): C, 61.59; H, 7.32; N, 2.99. Found (%): C, 61.06; H, 7.06; N, 2.98.

While the invention has been described in detail and with reference to specific embodiments thereof, it will be apparent to one skilled in the art that various changes and modifications can be made therein without departing from the spirit and scope thereof.

What is claimed is:

1. A compound represented by the following general formula (I)

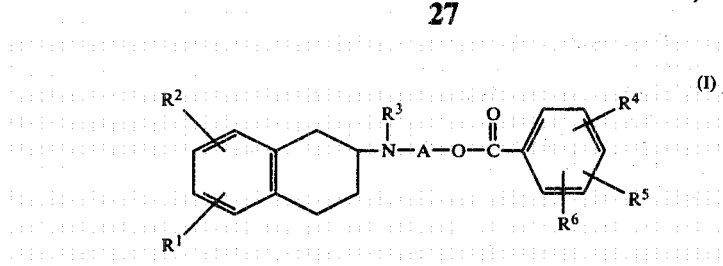

wherein $R^1$ and $R^2$, which may be the same or different, each represents a hydrogen atom, an alkoxy group or, when taken together, $R^1$ and $R^2$ represent an alkylenedioxy group; $R^3$ represents an alkyl group or a cycloalkyl group, $R^4$, $R^5$ and $R^6$, which may be the same or different, each represents a hydrogen atom, an alkoxy group, an alkyl group, a halogen atom, a hydroxyl group or, when two of $R^4$, $R^5$ and $R^6$ are taken together, they represent an alkylenedioxy group; and A represents a straight or branched chain alkylene group having 2 to 10 carbon atoms or an alkylene group having 2 to 10 carbon and interrupted with an oxygen atom forming an ether bond therein, and the therapeutically useful acid-addition salts thereof.

2. The compound according to claim 1 wherein the compound represented by the general formula (I) is represented by the following formula (I')

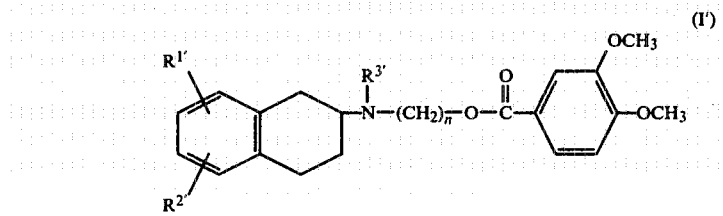

wherein $R^{1'}$ and $R^{2'}$, which may be the same or different, each represents a hydrogen atom or an alkoxy group; $R^{3'}$ represents an alkyl group; and n is either 4 or 6 and the therapeutically useful acid-addition salts thereof according to claim 1.

3. N-Ethyl-N-[4-(3,4-dimethoxybenzoyloxy)butyl]-1,2,3,4-tetrahydro-2-naphthylamine and the therapeutically useful acid-addition salts thereof, according to claim 1.

4. N-Ethyl-N-[6-(3,4-dimethoxybenzoyloxy)hexyl]-1,2,3,4-tetrahydro-2-naphthylamine and the therapeutically useful acid-addition salts thereof, according to claim 1.

5. N-Ethyl-N-[4-(3,4-dimethoxybenzoyloxy)butyl]-6-methoxy-1,2,3,4-tetrahydro-2-naphthylamine and the therapeutically useful acid-addition salts thereof, according to claim 1.

6. N-Ethyl-N-[6-(3,4-dimethoxybenzoyloxy)hexyl]-6-methoxy-1,2,3,4-tetrahydro-2-naphthylamine and the therapeutically useful acid-addition salts thereof, according to claim 1.

7. N-Propyl-N-[4-(3,4-dimethoxybenzoyloxy)butyl]-6-methoxy-1,2,3,4-tetrahydro-2-naphthylamine and the therapeutically useful acid-addition salts thereof, according to claim 1.

8. N-Isopropyl-N-[4-(3,4-dimethoxybenzoyloxy)butyl]-6-methoxy-1,2,3,4-tetrahydro-2-naphthylamine and the therapeutically useful acid-addition salts thereof, according to claim 1.

9. N-Ethyl-N-[4-(3,4-dimethoxybenzoyloxy)butyl]-6,7-dimethoxy-1,2,3,4-tetrahydro-2-naphthylamine and the therapeutically useful acid-addition salts thereof, according to claim 1.

10. N-Ethyl-N-[6-(3,4-dimethoxybenzoyloxy)hexyl]-6,7-dimethoxy-1,2,3,4-tetrahydro-2-naphthylamine and the therapeutically useful acid-addition salts thereof, according to claim 1.

11. N-Ethyl-N-[4-(3,4-dimethoxybenzoyloxy)butyl]-7-methoxy-1,2,3,4-tetrahydro-2-naphthylamine and the therapeutically useful acid-addition salts thereof, according to claim 1.

12. N-Ethyl-N-[4-(3,4-dimethoxybenzoyloxy)butyl]-8-methoxy-1,2,3,4-tetrahydro-2-naphthylamine and the therapeutically useful acid-addition salts thereof, according to claim 1.

* * * * *